United States Patent [19]

Maurer et al.

[11] 4,386,035
[45] May 31, 1983

[54] INTERMEDIATES FOR PREPARATION OF 3-BROMO-4-FLUORO-BENZYL ALCOHOL

[75] Inventors: Fritz Maurer, Wuppertal; Uwe Priesnitz, Solingen; Hans-Jochem Riebel; Rainer Fuchs, both of Wuppertal; Erich Klauke, Odenthal, all of Fed. Rep. of Germany

[73] Assignee: Bayer Aktiengesellschaft, Leverkusen, Fed. Rep. of Germany

[21] Appl. No.: 301,510

[22] Filed: Sep. 14, 1981

[30] Foreign Application Priority Data

Oct. 1, 1980 [DE] Fed. Rep. of Germany ....... 3036967

[51] Int. Cl.³ .............................................. C07C 69/96
[52] U.S. Cl. .................................. 260/463; 568/812; 560/103; 562/493
[58] Field of Search ...................... 562/493; 560/103; 260/463

[56] References Cited

PUBLICATIONS

Giri et al., Chemical Abstracts, vol. 71, (1969), 61,299s.
Degering, Organic Chemistry, (1951), 62–65, 204 & 205.

Primary Examiner—Bernard Helfin
Attorney, Agent, or Firm—Sprung, Horn, Kramer & Woods

[57] ABSTRACT

A process for the preparation of 3-bromo-4-fluoro-benzyl alcohol of the formula

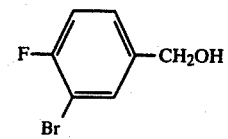

comprising reacting 3-bromo-4-fluoro-benzoic acid or a derivative thereof of the formula

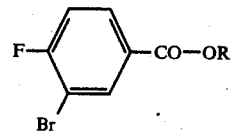

in which
  R is a hydrogen atom, an alkyl radical or an alkoxycarbonyl radical,
with a complex hydride of the formula

M(M'H₄)

in which
  M is lithium, sodium or potassium, and
  M' is boron or aluminum, at a temperature between about −20° and +150° C. When R is alkoxycarbonyl the starting material can be produced by reacting the corresponding free acid with a chloroformic acid ester. Compounds wherein R is alkyl or alkoxycarbonyl are new. The end product is a known intermediate for insecticides.

3 Claims, No Drawings

INTERMEDIATES FOR PREPARATION OF 3-BROMO-4-FLUORO-BENZYL ALCOHOL

The invention relates to an unobvious process for the preparation of 3-bromo-4-fluoro-benzyl alcohol and to new intermediate products for this process.

3-Bromo-4-fluoro-benzyl alcohol and its preparation are the subject of U.S. patent application Ser. No. 173,544, filed July 30, 1980 and now U.S. Pat. No. 4,326,087. According to that application, 3-bromo-4-fluoro-benzyl alcohol is prepared by reacting 3-bromo-4-fluoro-benzoyl fluoride with a complex hydride, such as sodium boranate, in the presence of a diluent, such as isopropanol, at a temperature between 0° and 50° C.

The present invention new provides a process for the preparation of 3-bromo-4-fluoro-benzyl alcohol of the formula

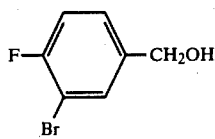
(I)

which is characterized in that (a) 3-bromo-4-fluoro-benzoic acid, or a derivative thereof, of the general formula

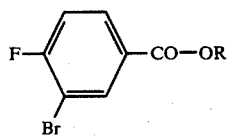
(II)

in which

R represents a hydrogen atom or an alkyl or alkoxycarbonyl group, is reacted with a complex hydride of the general formula

 (III)

in which

M represents lithium, sodium or potassium and

M' represents boron or aluminum, if appropriate in the presence of a catalyst and a diluent at a temperature between −20° and +150° C., or (b) where radical R in the compound of formula (II) represents hydrogen, the 3-bromo-4-fluoro-benzoic acid of the formula

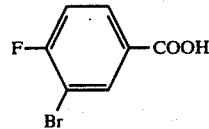
(II a)

is first reacted with a chloroformic acid ester of the general formula

 (IV)

in which $R^1$ represents an alkyl group, if appropriate in the presence of an acid acceptor and a diluent, at a temperature between −20° and +50° C., and the resulting mixed anhydride of the general formula

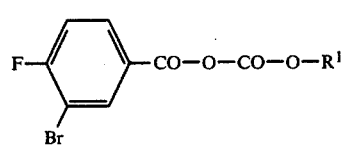
(II b)

in which $R^1$ has the abovementioned meaning, is then reacted with the complex hydrides of the formula (III), as defined above, if appropriate in the presence of a catalyst and a diluent, at a temperature between −20° and +150° C.

The present invention further provides, as new compounds, the 3-bromo-4-fluoro-benzoic acid derivatives of the general formula

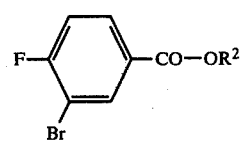
(II c)

in which $R^2$ represents an alkyl or alkoxycarbonyl group.

The new intermediate products of the present invention of the formula (II c) are obtained when 3-bromo-4-fluoro-benzoic acid, or a reactive derivative thereof, is reacted with an alcohol or a chloroformic acid ester, if appropriate in the presence of catalysts, acid acceptors and diluents.

Surprisingly, 3-bromo-4-fluoro-benzyl alcohol can be prepared in very good yields and in a high purity from 3-bromo-4-fluoro-benzoic acid and its derivatives of the formula (II) by the process according to the invention.

The advantages of the new process are that the starting compound 3-bromo-4-fluoro-benzoic acid can be obtained in a high yield by a simple process, and that the new process likewise can be carried out with a small degree of technical effort, using inexpensive auxiliaries and reactants, and gives high yields.

The reaction variants (a) and (b) of the process according to the invention are illustrated by the following equation, in which 3-bromo-4-fluoro-beenzoic acid ethyl ester and lithium alanate are used as starting materials for reaction variant (a), or the mixed anhydride of 3-bromo-4-fluoro-benzoic acid and methyl carbonate together with potassium boranate are used as starting materials for reaction variant (b):

reaction variant (a)

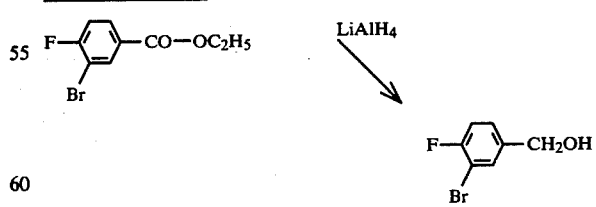

reaction variant (b)

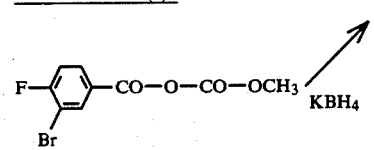

The abovementioned reaction variant (a) of the process according to the present invention is preferably carried out using diluents. Possible diluents are, in particular, ethers (such as diethyl ether, dipropyl ether and dibutyl ether, glycol dimethyl ether and diglycol dimethyl ether (diglyme)), tetrahydrofuran and dioxane.

It is also possible to carry out the process according to the invention in a two-phase system of water and one of the abovementioned ethers. In this case, phase transfer catalysts are preferably used. Examples of these are triethylbenzylammonium bromide ("TEBA"), tetrabutylammonium bromide, benzyl-triethylammonium bisulphate and methyltrioctyl-ammonium chloride ("Aliquat 336").

If the reaction is carried out in an anhydrous solvent, a catalyst selected from the so-called Lewis acids (such as boron trifluoride, zinc chloride or aluminum chloride) is preferably used. Aluminum chloride is particularly preferred as a catalyst.

Complex hydrides of the formula (III) which can be used in the process according to the invention are, for example, lithium alanate (lithium tetrahydridoaluminate) and sodium boranate (sodium tetrahydridoborate). The latter is particularly preferred.

Reaction variant (a) of the process according to the invention is carried out at a temperature between about $-20°$ and $+150°$ C., preferably at a temperature between about $0°$ and $100°$ C., and usually under normal pressure, that is to say between about 0.1 and 10 bars, preferably between about 0.5 and 5 bars.

Between about 0.5 and 2 moles, preferably between about 0.6 and 1.5 moles, of complex hydride of the formula (III) and between about 0.1 and 1 mole, preferably between about 0.2 and 0.5 mole of catalyst are employed per mole of 3-bromo-4-fluoro-benzoic acid, or a derivative thereof, of the formula (II).

In a preferred embodiment of reaction variant (a), the starting compound of the formula (II) is initially introduced into the reaction vessel in one of the abovementioned diluents, and the complex hydride of the formula (III) and the catalyst are added thereto successively or simultaneously. The reaction mixture is stirred until the reaction has ended.

Working up can be carried out by customary methods. For example, the mixture is diluted with (ice-)water and acidified (for example with hydrochloric acid). The 3-bromo-4-fluoro-benzyl alcohol thereby separates out as an oily crude product, which can be purified by vacuum distillation. In another variant of working up, the crude product, after acidification, is extracted with an organic solvent which is virtually immiscible with water (such as methyl tert.-butyl ether), and, after the organic phase has been washed and dried, the product is isolated by distillation.

Preferred chloroformic acid esters of formula (IV) to be used as reactants in reaction variant (b) are those in which $R^1$ represents a $C_1$ to $C_4$ alkyl group, in particular a methyl or ethyl group.

Examples which may be mentioned are chloroformic acid methyl ester and chloroformic acid ethyl ester.

The abovementioned reaction variant (b) of the process according to the invention is preferably carried out using diluents such as are mentioned above for variant (a).

The first stage of reaction variant (b) is preferably carried out in the presence of an acid acceptor. Acid acceptors which can be used are virtually any of the customary acid-binding agents. Amines such as trimethylamine, triethylamine, dimethylaniline, dimethylbenzylamine, pyridine, diazabicyclononene and diazabicycloundecene have proved particularly suitable.

The reaction temperature is kept between about $-20°$ and $+50°$ C., preferably between about $0°$ and $30°$ C., in the first stage of reaction variant (b). The process is in general carried out under normal pressure.

Between about 0.8 and 1.5 moles, preferably between about 0.95 and 1.2 moles, of chloroformic acid ester of the formula (IV) and between about 0.8 and 1.5 moles, preferably between about 0.95 and 1.2 moles, of acid-binding agent are employed per mole of 3-bromo-4-fluoro-benzoic acid.

In a preferred embodiment of reaction variant (b), the 3-bromo-4-fluoro-benzoic acid together with the acid-binding agent are initially introduced into the reaction vessel in one of the abovementioned diluents, and the chloroformic acid ester of the formula (IV) is slowly added thereto.

The reaction mixture is stirred until the reaction has ended and is then filtered, if appropriate under increased or reduced pressure. The intermediate of the formula (II b) can be isolated from the filtrate by customary methods. Preferably, however, the filtrate is used for the further reaction: for example, a phase transfer catalyst is added, and an aqueous solution of sodium boranate is slowly added. When the reaction has ended, the mixture is acidified and the organic phase is separated off, washed, dried, filtered and concentrated, 3-bromo-4-fluoro-benzyl alcohol being obtained as the residue in the form of a colorless oil.

Alternatively, the filtrate, which contains the compound of the formula (II b) can also be reacted as described above for reaction variant (a).

Preferred novel 3-bromo-4-fluoro-benzoic acid derivatives of the formula (II c) according to the present invention are those in which $R^2$ represents a $C_1$ to $C_4$ alkyl or ($C_1$ to $C_4$ alkoxy)-carbonyl radical. Examples which may be mentioned are: 3-bromo-4-fluoro-benzoic acid methyl ester, ethyl ester, n- and iso- propyl ester and n-, iso-, sec.- and tert.-butyl ester, and the anhydrides of 3-bromo-4-fluoro-benzoic acid and methyl carbonate and of 3-bromo-4-fluoro-benzoic acid and ethyl carbonate.

The compounds of the formula (II c) in which $R^2$ represents an alkoxycarbonyl group are obtained by reacting 3-bromo-4-fluoro-benzoic acid with chloroformic acid esters of the formula (IV), if appropriate in the presence of an acid acceptor (such as dimethylbenzylamine), and if appropriate using a diluent (such as carbon tetrachloride), at a temperature between about $-20°$ and $+50°$ C. (compare reaction variant (b) above). The products of the formula (II c) can be isolated by filtering the mixture, when the reaction has ended, and distilling off the solvent from the filtrate.

The 3-bromo-4-fluoro-benzoic acid alkyl esters of the formula (II c) are obtained, for example, when (i) 3-bromo-4-fluoro-benzoic acid is reacted with a corresponding alcohol, if appropriate in the presence of a catalyst (such as sulphuric acid), or (ii) a reactive derivative of 3-bromo-4-fluoro-benzoic acid (such as 3-bromo-4-fluoro-benzoyl fluoride), is reacted with a corresponding alcohol, if appropriate in the presence of a catalyst (such as pyridine).

In each of these reaction variants (i) and (ii), the reaction temperature is between about $20°$ and $100°$ C.

In both variants, (i) and (ii), working up can be carried out in the customary manner, for example by distillation of the reaction mixture after the reaction. It is also possible, after distilling off the alcohol, for the residue first to be taken up in a water-immiscible solvent (such as toluene), and for the solution to be washed with water, dried, filtered and then distilled.

The 3-bromo-4-fluoro-benzyl alcohol to be prepared by the process according to the invention can be used as an intermediate product for the preparation of insecticides (see U.S. application Ser. No. 173,544, supra).

For this preparation, 3-bromo-4-fluoro-benzyl alcohol is first etherified by reaction with benzyl chloride in the presence of a base (such as potassium tert.-butylate) and a diluent (such as tetrahydrofuran) at a temperature between 20° and 80° C.; the 3-bromo-4-fluoro-benzyl benzyl ether obtained in this manner is reacted with a phenolate (such as sodium phenolate) in the presence of a catalyst (such as copper-I oxide) and a diluent (such as isoquinoline) at a temperature between 140° and 180° C., and the 4-fluoro-3-phenoxy-benzyl benzyl ether thus obtained is converted into 4-fluoro-3-phenoxy-benzyl bromide by known methods of splitting ethers, for example by heating with hydrobromic acid.

4-Fluoro-3-phenoxy-benzyl bromide is already known as an intermediate product for insecticides (see U.S. Pat. No. 4,218,469).

PREPARATE EXAMPLES

Example 1

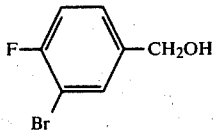

Reduction of 4-fluoro-3-bromobenzoic acid:

6.7 g of aluminum chloride were added to a solution of 10.9 g of 95% pure 3-bromo-4-fluorobenzoic acid in 150 ml of diglyme at 20° C. The reaction mixture was subsequently stirred at 20° C. for 10 minutes and 5.7 g of sodium borohydride were then added in portions at 20° to 25° C. After 12 hours, about 100 ml of water (vigorous foaming) and then about 1 ml of 10% strength hydrochloric acid were added dropwise. About 100 ml of tert.-butyl methyl ether were added and the organic phase was separated off. It was washed once with about 30 ml of saturated sodium bicarbonate solution. The ether phase was then concentrated. 6.7 g (76% of theory) of 4-fluoro-3-bromo-benzyl alcohol were obtained.

The sodium bicarbonate solution was acidified. 1 g of unreacted 4-fluoro-3-bromobenzoic acid precipitated and was filtered off and dried in air.

According to the $^1$H-nuclear magnetic resonance spectrum, the acid recovered was of the same quality as the acid employed.

EXAMPLE 2

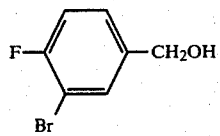

10.8 g of chloroformic acid ethyl ester were added dropwise to a solution of 20.8 g of 95% pure 4-fluoro-3-bromo-benzoic acid and 13.5 g of dimethylbenzylamine in 200 ml of diethyl ether at 0° C. Stirring was continued at 0° to 20° C. for 1 hour and the hydrochloride which had precipitated was then filtered off. After adding 0.1 g of triethylbenzylammonium bromide, a solution of 7.6 g of sodium borohydride in 50 ml of water was added dropwise to the filtrate at 20° C. The reaction mixture was subsequently stirred at 20° C. for 3 hours and was then acidified with dilute hydrochloric acid. The ether phase was separated off and washed once with 30 ml of saturated sodium bicarbonate solution. The ether phase was then concentrated. 17.3 g (93.4% of theory) of 4-fluoro-3-bromobenzyl alcohol were thus obtained in the form of a colorless oil.

The sodium bicarbonate solution was acidified. The unreacted 4-fluoro-3-bromobenzoic acid precipitated and was filtered off and dried in air. 1 g of 4-fluoro-3-bromo-benzoic acid which, according to the $^1$H-nuclear magnetic resonance spectrum, was of the same quality as the acid employed was obtained.

The reaction could also be carried out in methyl t-butyl ether instead of in diethyl ether.

EXAMPLE 3

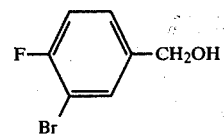

4-Fluoro-3-bromo-benzyl alcohol from fluorobromobenzoic acid methyl ester:

First 3.8 g (0.1 mole) of sodium borohydride and then 4.5 g (0.033 mole) of aluminum chloride were added in portions to a solution of 23.3 g (0.1 mole) of 4-fluoro-3-bromobenzoic acid methyl ester in 50 ml of diglyme at 5° C. The mixture was subsequently stirred, without cooling, until the exothermic reaction had ended (a rise in temperature up to about 50° C.) and the reaction was then allowed to go to completion in the course of 1 hour at 100° C. The reaction solution was then poured onto a mixture of 125 ml of icewater and 12 ml of concentrated hydrochloric acid and the benzyl alcohol which had separated out was separated off and distilled in vacuo. 18.7 g (91% of theory) of 4-fluoro-3-bromobenzyl alcohol were obtained in this manner as a colorless oil with a boiling point of 65° to 70° C. (0.1 mbar). "One-pot process"

2 g of triethylamine, dissolved in 5 ml of tetrahydrofuran, were added dropwise to a solution of 4.2 g of 3-bromo-4-fluoro-benzoic acid and 1.95 g of chloroformic acid methyl ester in 30 ml of tetrahydrofuran at 20° C., while stirring. Stirring was continued for a further 40 minutes at 20°–25° C. and the hydrochloride which had precipitated was then filtered off. 5.5 g of sodium borohydride, dissolved in 20 ml of water, were added dropwise to the filtrate at 10° to 20° C., while stirring. Stirring was then continued for a further 4 hours at 20° C. The reaction batch was subsequently poured into 100 ml of water and extracted by shaking with 80 ml of methylene chloride. The methylene chloride phase was separated off and dried over magnesium sulphate and the solvent was then distilled off in vacuo. 1.95 g (95% of theory) of 3-bromo-4-fluoro-benzyl alcohol were obtained as a colorless oil.

EXAMPLE 4

Preparation of the mixed anhydride of 4-fluoro-3-bromo-benzoic acid and ethyl carbonate:

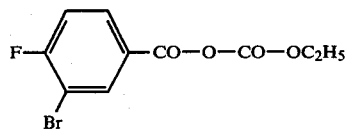

First 7.6 g (0.05 mole) of dimethylbenzylamine and then 5.4 g (0.05 mole) of chloroformic acid ethyl ester were added dropwise to a solution of 10.9 g (0.05 mole) of 4-fluoro-3-bromo-benzoic acid in 150 ml of carbon tetrachloride at 0° C. The mixture was subsequently stirred at 0° C. for 30 minutes and the hydrochloride formed was then filtered off. A nuclear magnetic resonance spectrum proved the presence of the abovementioned compound.

From chloroformic acid methyl ester chloride and 4-fluoro-3-bromo-benzoic acid, the corresponding anhydride of the formula

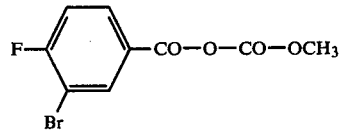

could also be prepared in the same manner.

EXAMPLE 5

(a) Preparation of 4-fluoro-3-bromobenzoic acid methyl ester from fluorobromobenzoic acid:

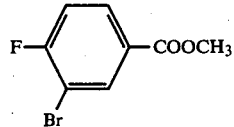

A mixture of 87.6 g (0.38 mole) of 95% pure 4-fluoro-3-bromo-benzoic acid, 200 ml of methanol and 3 ml of sulphuric acid was boiled under for 18 hours. The excess methanol was then distilled off in vacuo, 300 ml of toluene were added and the solution was shaken first with 50 ml of water, then with 50 ml of saturated sodium bicarbonate solution and subsequently with 50 ml of water again. Thereafter, the solvent was distilled off in vacuo and the residue was distilled in vacuo. 86 g (97% of theory) of 4-fluoro-3-bromo-benzoic acid methyl ester were obtained in this manner in the form of a colorless oil which solidified as crystals when cold and had a boiling point of 64° C./0.1 mm Hg.

(b) Preparation from fluorobromobenzoyl fluoride:

221 g (1 mole) of 4-fluoro-3-bromobenzoyl fluoride were added dropwise to a mixture of 96 g (3 moles) of methanol and 1 g of pyridine. The reaction mixture was then boiled for a further 2 hours under reflux and was subsequently worked up by distillation. 217 g (93% of theory) of 4-fluoro-3-bromobenzoic acid methyl ester were thus obtained in the form of a colorless oil which solidified when cold and had a boiling point of 124° C./22 mm Hg (melting point 29° to 30° C.).

It will be understood that the specification and examples are illustrative but not limitative of the present invention and that other embodiments within the spirit and scope of the invention will suggest themselves to those skilled in the art.

We claim:

1. A 3-bromo-4-fluoro-benzoic acid derivative of the formula

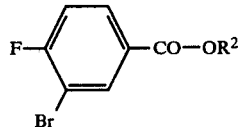

in which $R^2$ is an alkoxycarbonyl group.

2. A compound according to claim 1, in which $R^2$ is a ($C_1$ to $C_4$ alkoxy)-carbonyl radical.

3. A compound according to claim 1, in which $R^2$ is methoxycarbonyl or ethoxycarbonyl.

* * * * *